(12) United States Patent
Ohnishi et al.

(10) Patent No.: US 7,195,925 B2
(45) Date of Patent: Mar. 27, 2007

(54) POLYMER HAVING AN UPPER CRITICAL SOLUTION TEMPERATURE

(75) Inventors: Noriyuki Ohnishi, Yokohama (JP); Hirotaka Furukawa, Yokohama (JP); Kazunori Kataoka, Tokyo (JP); Katsuhiko Ueno, Tsukuba (JP)

(73) Assignees: National Institute of Advanced Industrial Science and Technology, Tokyo (JP); Chisso Corporation, Osaka (JP)

( * ) Notice: Subject to any disclaimer, the term of this patent is extended or adjusted under 35 U.S.C. 154(b) by 365 days.

(21) Appl. No.: 10/362,173

(22) PCT Filed: Aug. 20, 2001

(86) PCT No.: PCT/JP01/07121

§ 371 (c)(1), (2), (4) Date: Feb. 21, 2003

(87) PCT Pub. No.: WO02/16454

PCT Pub. Date: Feb. 28, 2002

(65) Prior Publication Data

US 2003/0186293 A1   Oct. 2, 2003

(30) Foreign Application Priority Data

Aug. 21, 2000 (JP) .............................. 2000-249818

(51) Int. Cl.
- G01N 33/545 (2006.01)
- C07K 17/08 (2006.01)
- C12N 11/08 (2006.01)
- C07D 495/04 (2006.01)
- C08F 20/56 (2006.01)
- A61K 47/48 (2006.01)

(52) U.S. Cl. ................... 436/531; 436/532; 435/6; 435/7.5; 435/7.72; 435/188; 522/175; 530/815

(58) Field of Classification Search ............. 436/532, 436/531; 435/7.5, 6, 7.72, 188; 524/175; 522/175; 530/815

See application file for complete search history.

(56) References Cited

U.S. PATENT DOCUMENTS 4,157,418 A * 6/1979 Heilmann ............ 428/355 CN
5,750,357 A * 5/1998 Olstein et al. ............ 435/7.32

FOREIGN PATENT DOCUMENTS

| EP | 0 922 715 | 6/1999 |
|---|---|---|
| JP | 60-231644 | 11/1985 |
| JP | 4-213311 | 8/1992 |
| WO | 01/09141 | 2/2001 |
| WO | 2005/050224 | 6/2005 |

OTHER PUBLICATIONS

O'Callaghan et al. BirA enzyme: production and application in the study of membrane receptor-ligand interaction by site-specific biotinylation. Analytical Biochemistry 1999, vol. 266, pp. 9-15.*

* cited by examiner

*Primary Examiner*—Long V. Le
*Assistant Examiner*—Shafiqul Haq
(74) *Attorney, Agent, or Firm*—Wenderoth, Lind & Ponack, LLP

(57) ABSTRACT

The invention relates to a stimulus-responding polymer obtained by polymerizing at least a monomer represented by a general formula (1) and a monomer represented by a general formula (2), and a separation method or concentration method of microorganisms, a purification method, detection method or concentration method of nucleic acids, a separating agent, a separation method of biomaterials and a conversion method of materials, which use this polymer, General formula (1)

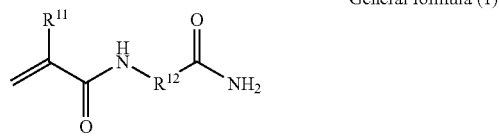

(in the formula, $R^{11}$ represents hydrogen atom or methyl group, and $R^{12}$ represents single bond or a straight or branched alkylene group having from 1 to 5 carbon atoms)

General formula (2)

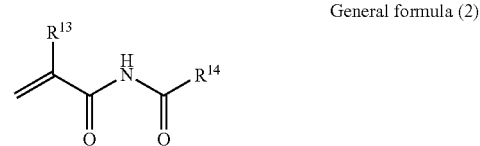

(in the formula, $R^{13}$ represents hydrogen atom or methyl group, and $R^{14}$ represents hydrogen atom, a straight, branched or cyclic alkyl group, alkoxyl group or alkylamino group having from 1 to 10 carbon atoms, an aryl group or a heterocyclic group).

32 Claims, No Drawings

POLYMER HAVING AN UPPER CRITICAL SOLUTION TEMPERATURE

This application is a National Stage Application of PCT/JP01/07121, filed Aug. 20, 2001.

TECHNICAL FIELD

This invention relates to a stimulus-responding polymer, a separation method or concentration method of microorganisms, a purification method, detection method or concentration method of nucleic acids, a separating agent, a separation method of biomaterials and a conversion method of materials.

BACKGROUND ART

In recent years, stimulus-responding polymers are broadly applied to drug delivery systems (DDS), various types of separating agents, catheters, artificial muscles, chemovalves and the like, and their importance is rapidly increasing. For example, Japanese Patent Laid-Open No. 103653/1996 describes poly-N-isopropylacrylamide, N,N-diethylacrylamide and the like acrylamide derivatives and polymethylvinyl ether and the like vinyl ethers as stimulus-responding polymers which swell or contract in an aqueous solution by changing their higher-order structures through the stimulus of heat, pH, potential, light or the like.

However, though it is described that known polymers which swell or contract by responding to temperature changes have upper critical solution temperature (to be referred to as "UCST" hereinafter) or lower critical solution temperature (to be referred to as "LCST" hereinafter), all of them are polymers having LCST in reality. That is, they have a property to become insoluble in water at a certain temperature or more by reversibly causing aggregation between polymers but becomes soluble in water at less than that.

Since polymers having LCST become insoluble in water at a certain temperature or more by contraction of the polymers, there is a problem in that a demand for carrying out the contraction under a low temperature by a temperature falling operation is difficult to control, in applying them to separating agents and the like uses. For example, when used as separating agents for proteins and the like which are unstable to heat, the polymers having LCST aggregate by a temperature rising operation, so that it is necessary to take into consideration a danger of accompanying denaturation of protein by the operation.

On the other hand, in inter-polymer ion complex, polysoap and the like which use polyacrylic acid as a polymer that shows UCST in a aqueous solution, they do not show the UCST in some cases due to ion dissociation when they are used in a buffer solution for, e.g., separating agent and the like uses.

DISCLOSURE OF THE INVENTION

Taking the aforementioned problems involved in the prior art into consideration, the present inventors have made intensive efforts and found as a result that a polymer obtained by polymerizing at least a monomer represented by the following general formula (1) and a monomer represented by the general formula (2) has UCST even in a buffer solution, and that separation or concentration of microorganisms, purification, detection or concentration of nucleic acids, separation of biomaterials and conversion of materials can be carried out efficiently when the polymer of the invention is used, and the invention has been accomplished based on these findings.

The invention has the following construction.

(1) A polymer obtained by polymerizing at least a monomer represented by the general formula (1) and a monomer represented by the general formula (2);

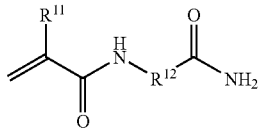

General formula (1)

(in the formula, $R^{11}$ represents hydrogen atom or methyl group, and $R^{12}$ represents single bond or a straight or branched alkylene group having from 1 to 5 carbon atoms)

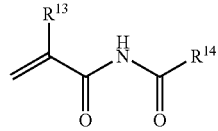

General formula (2)

(in the formula, $R^{13}$ represents hydrogen atom or methyl group, and $R^{14}$ represents hydrogen atom, a straight, branched or cyclic alkyl group, alkoxyl group or alkylamino group having from 1 to 10 carbon atoms, an aryl group or a heterocyclic group).

(2) A polymer obtained by polymerizing a monomer represented by the aforementioned general formula (1) and a monomer having a biotin moiety.

(3) The polymer described in the aforementioned item 1 or 2, wherein one or more species selected from hydrophilic monomers and hydrophobic monomers are further used.

(4) The polymer described in any one of the aforementioned items 1 to 3, wherein one of a pair of substances mutually having specific action is immobilized.

(5) The polymer described in the aforementioned item 4, wherein the pair of substances mutually having specific action are one or more pairs selected from the combinations of biotin and avidin, an antigen and its antibody, a polynucleotide and another polynucleotide having a complementary nucleotide sequence, cDNA and mRNA, an enzyme (active site) and its substrate, an enzyme (active site) and its product, an enzyme (active site) and its competitive inhibitor, an enzyme (coenzyme binding site) and its coenzyme, an enzyme (coenzyme binding site) and a triazine pigment, a protease and a protease inhibitor, an Fc region and protein A, an Fc region and protein G, lectin and a saccharide, a hormone receptor and the hormone, DNA and a DNA binding protein, heparin and fibronectin, and heparin and laminin.

(6) The polymer described in the aforementioned item 4, wherein the pair of substances mutually having specific action are biotin and avidin.

(7) The polymer described in the aforementioned item 4, wherein one of said pair of substances, immobilized to the polymer, is biotin.

(8) The polymer described in the aforementioned item 7, wherein the biotin is biotin linked to avidin (to be referred to as "avidin-linked biotin" hereinafter).

(9) The polymer described in the aforementioned item 7, wherein an avidinylation enzyme is linked to biotin.

(10) The polymer described in the aforementioned item 8, wherein a biotinylation enzyme is linked to avidin-linked biotin.

(11) A method for converting a substance, characterized in that the polymer described in the aforementioned item 9 or 10 is used.

(12) The polymer described in the aforementioned item 7, wherein an avidinylated antibody is linked to biotin.

(13) The polymer described in the aforementioned item 8, wherein a biotinylated antibody is linked to avidin-linked biotin.

(14) A method for separating or a method for concentrating a microorganism, characterized in that the polymer described in the aforementioned item 12 or 13 is used.

(15) The polymer described in the aforementioned item 7, wherein an avidinylated molecular chaperone is linked to biotin.

(16) The polymer described in the aforementioned item 8, wherein a biotinylated molecular chaperone is linked to avidin-linked biotin.

(17) A method for reforming a denatured protein, characterized in that the polymer described in the aforementioned item 15 or 16 is used.

(18) The polymer described in the aforementioned item 7, wherein an avidinylated heat shock protein is linked to biotin.

(19) The polymer described in the aforementioned item 8, wherein a biotinylated heat shock protein is linked to avidin-linked biotin.

(20) A method for reforming a denatured protein, characterized in that the polymer described in the aforementioned item 19 or 20 is used.

(21) The polymer described in the aforementioned item 7, wherein an avidinylated nucleic acid is linked to biotin.

(22) The polymer described in the aforementioned item 8, wherein a biotinylated nucleic acid is linked to avidin-linked biotin.

(23) A method for purifying, detecting or concentrating a nucleic acid, characterized in that the polymer described in the aforementioned item 21 or 22 is used.

(24) A method for detecting a nucleic acid, characterized in that a nucleic acid obtained by the purification or concentration method of a nucleic acid described in the aforementioned item 23 is amplified.

(25) The method for detecting a nucleic acid described in the aforementioned item 24, wherein the amplifying method is a PCR method or an RT-PCR method.

(26) A separating agent which contains the polymer described in any one of the aforementioned items 1 to 8.

(27) A method for separating a biomaterial, characterized in that the separating agent described in the aforementioned item 26 is used.

BEST MODE FOR CARRYING OUT THE INVENTION

The following describes the invention further in detail.

The polymer having upper critical temperature (to be referred to as "UCST" hereinafter), (to be referred to as "UCST polymer" hereinafter), is a polymer having such a property that, in a solvent containing said polymer, said polymer becomes a dissolved state in the solvent when temperature of said solvent containing the polymer exceeds a specified temperature but said polymer precipitates and aggregates in the solvent at a temperature equal to or lower than said specified temperature. The UCST means said specified temperature. Also, the phenomena of causing dissolution and precipitation of a polymer bordering the UCST is called UCST characteristics.

Though the aforementioned solvent is not particularly limited, water and a liquid containing 50% by weight or more of water can be illustratively cited. As the liquid containing 50% by weight or more of water, physiological saline, buffer solutions and the like can be illustratively cited. Also, said solvent may be a mixed solution of acetone or the like organic solvent with water, with the proviso that it shows the UCST characteristics under a state of containing the polymer.

A first polymer of the invention is a UCST polymer obtained by polymerizing at least a monomer represented by the general formula (1) (to be referred to as "monomer (1)" hereinafter) and a monomer represented by the general formula (2) (to be referred to as "monomer (2)" hereinafter).

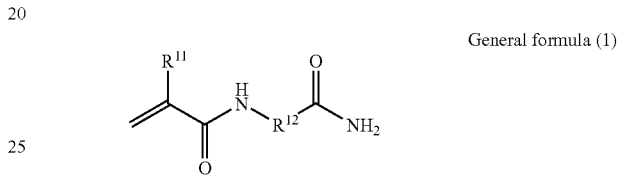

General formula (1)

In the general formula (1), $R^{11}$ represents hydrogen atom or methyl group, and it is desirable that $R^{11}$ is hydrogen atom according to the invention. $R^{12}$ represents single bond or a straight or branched chain alkylene group having from 1 to 5 carbon atoms, and it is desirable that $R^{12}$ is ethylene group according to the invention.

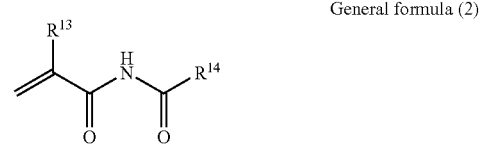

General formula (2)

In the general formula (2), $R^{13}$ represents hydrogen atom or methyl group, and it is desirable that $R^{13}$ is hydrogen atom according to the invention. $R^{14}$ represents hydrogen atom, a straight, branched or cyclic alkyl group, alkoxyl group or alkylamino group having from 1 to 10 carbon atoms, an aryl group or a heterocyclic group. A straight chain alkyl group having from 1 to 5 carbon atoms is desirable as the alkyl group, and a straight chain alkyl group having from 1 to 5 carbon atoms is desirable as the alkyl group moiety of the alkoxyl group and alkylamino group. Phenyl group, naphthyl group and the like can be exemplified as the aryl group, and pyrimidine or the like can be exemplified as a group which forms the heterocyclic group.

When one or more species selected from hydrophilic monomers and hydrophobic monomers are used as components other than the monomer (1) and monomer (2) in carrying out polymerization of the UCST polymer of the invention, it is possible to control UCST by changing their kinds and using ratio.

Classification of the monomers to be used as the other components into hydrophilic and hydrophobic monomers is carried out based on the hydrophilic property of the monomer (1). That is, those having higher hydrophilic property than the monomer (1) to be used in the polymerization are hydrophilic monomers and those having higher hydrophobic property are hydrophobic monomers. Also, when two or more species of the monomer (1) are used in the polymerization, the classification may be carried out based on the most hydrophilic monomer among them.

Though they vary depending on the kinds of the monomer (1) to be used in the polymerization and thus cannot be generally defined, illustrative examples of the hydrophilic monomers to be used in the invention include (meth)acrylamide, (meth)acrylic acid, allyl alcohol, allylamine and the like, and those of the hydrophobic monomers include an alkyl (meth)acrylate, styrene, ethylene, propylene, acetylene and the like unsaturated hydrocarbons, an alkyl vinyl ether, an alkyl (meth)acrylamide and the like.

When a hydrophilic monomer is used in the polymerization of the UCST polymer of the invention, UCST shows a reducing tendency, and when a hydrophobic monomer is used on the contrary, UCST shows an increasing tendency.

The composition of respective monomers in polymerizing the UCST polymer of the invention is not particularly limited, but it is generally monomer (1): monomer (2): other monomer molar ratio=95 to 20:1 to 60:0 to 40, preferably 95 to 50:1 to 50:0 to 20.

Regarding a reaction solution containing the UCST polymer of the invention just after the polymerization, unreacted monomers, salts and the like impurities are present in the reaction solution. Elimination of the impurities may be carried out by dialysis, or it may be carried out by setting temperature of the solution to UCST or less to effect aggregation, recovering the aggregates and then removing the supernatant.

A second polymer of the invention is a UCST polymer obtained by polymerizing the aforementioned monomer (1) with a monomer having a biotin moiety. Since the second UCST polymer of the invention can specifically adsorb avidin through the biotin moiety introduced into said UCST polymer, the use of said UCST polymer renders possible efficient separation, purification and concentration of various substances of interest by avidinylating said substances of interest.

Among the monomer (1), acryloylglycine amide represented by the following general formula (3) can be used preferably in the second UCST polymer of the invention.

General formula (3)

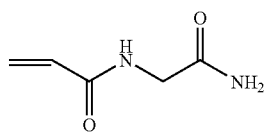

According to the invention, the monomer to be used in the invention having a biotin moiety is not particularly limited and (meth)acrylamide, (meth)acrylate derivatives and the like which use the terminal carboxyl group of biotin can be exemplified as monomers having biotin as a part of their structures, though not limited thereto in the invention. As preferred examples of said monomer among them, polymerizable biotin derivatives represented by the following general formula (4) can be cited.

General formula (4)

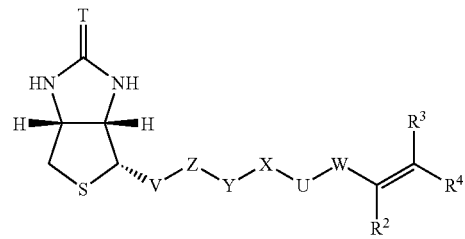

In the general formula (4), $R^2$ represents hydrogen atom or an alkyl group. $R^3$ and $R^4$ each independently represents hydrogen atom, an alkyl group or an aryl group. T represents oxygen atom or =NH group. W represents single bond or carbonyl group, thiocarbonyl group or an alkylene group having from 1 to 5 carbon atoms. U represents single bond or —NH— group. X represents single bond or hydrocarbon bond having from 1 to 8 carbon atoms, oxygen atom or —NH— group. Y represents single bond or carbonyl group, thiocarbonyl group, —NH— group, 1,2-dioxyethylene group or 1,2-diaminoethylene group. Z represents single bond or carbonyl group, thiocarbonyl group, an alkylene group having from 1 to 5 carbon atoms, oxygen atom or —NH— group. V represents single bond or an alkylene group having from 1 to 5 carbon atoms.

Among the polymerizable biotin derivatives represented by the general formula (4), polymerizable biotin derivatives represented by the following general formulae (5) to (7) can be used desirably in the UCST polymer of the invention.

General formula (5)

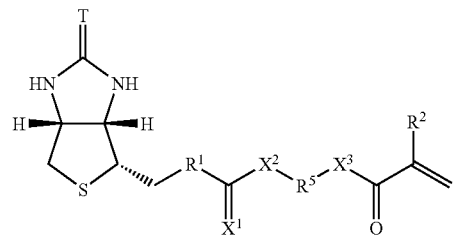

General formula (6)

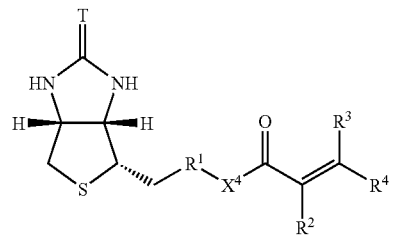

General formula (7)

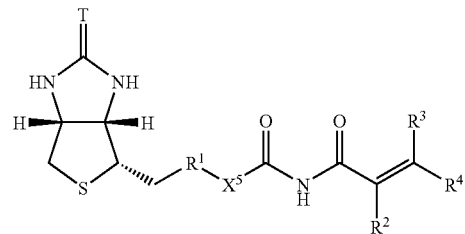

In the general formulae (5) to (7), $R^1$ represents single bond or an alkylene group having from 1 to 4 carbon atoms, and $R^5$ represents an alkylene group having 2 or 3 carbon atoms. $X^1$ represents oxygen atom or sulfur atom, and $X^2$ to $X^5$ each independently represents oxygen atom or —NH— group. T, $R^2$, $R^3$ and $R^4$ are as defined in the aforementioned general formula (4).

The polymerizable biotin derivative represented by the aforementioned general formula (5) can be obtained by converting the side chain carboxyl hydroxyl group of a biotin derivative represented by the following general formula (8) into an appropriate leaving group and then allowing it to undergo a condensation reaction with an acryl derivative represented by the following general formula (9).

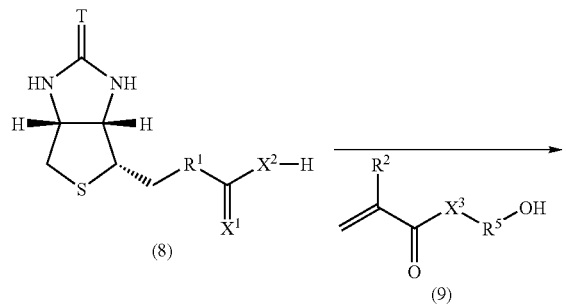

The polymerizable biotin derivative represented by the aforementioned general formula (6) can be obtained generally by allowing a biotin derivative represented by the following general formula (10) to react with an appropriate acrylation agent (including a methacrylation agent, and their examples include acrylic acid, acrylic acid chloride, acrylic anhydride, acryloxy succinimide and the like acrylation agents and methacrylic acid, methacrylic acid chloride, methacrylic anhydride, methacryloxy succinimide and the like methacrylation agents).

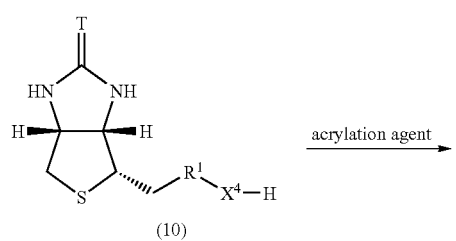

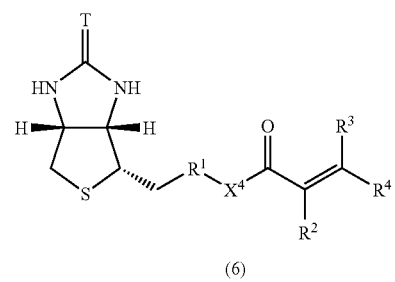

In this case, the biotin derivative represented by the general formula (10) can be obtained by converting the hydroxyl group of an alcohol compound ($X^4$=oxygen atom) obtained by reducing a biotin derivative represented by the general formula (8) with an appropriate reducing agent into a functional group having a leaving group function, and then subjecting said alcohol compound after the conversion and an amine derivative ($X^4$=—NH—) to a substitution reaction.

The polymerizable biotin derivative represented by the aforementioned general formula (7) can be obtained generally by allowing a biotin derivative represented by the following general formula (11) to react with an isocyanate compound represented by the general formula (12) in tetrahydrofuran (THF), dimethyl sulfoxide (DMSO), ether, dimethylformamide (DMF), dichloromethane, chloroform, ethyl acetate, acetone, an aliphatic hydrocarbon, benzene, toluene or the like aprotic solvent.

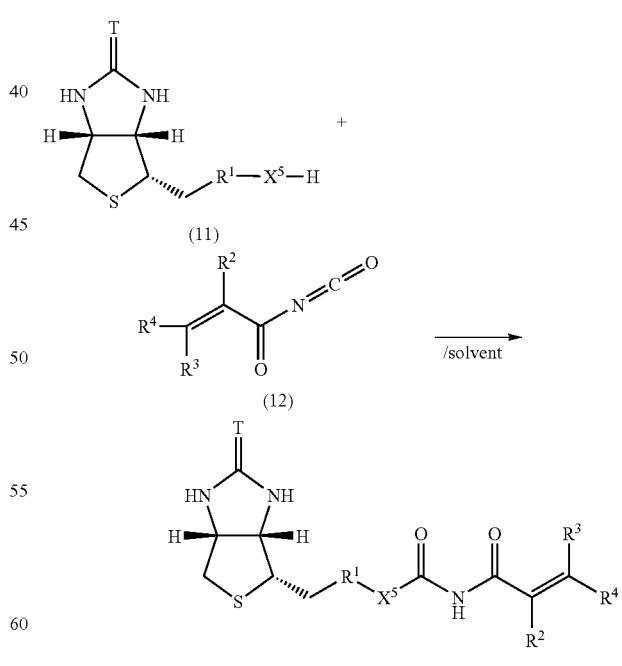

In addition, a polymerizable biotin derivative represented by the following general formula (13) can be used particularly preferably in the UCST polymer of the invention.

General formula (13)

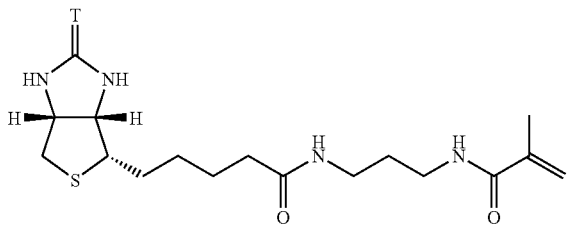

Also included as monomers which can be used preferably in the UCST polymer of the invention are a biotin methacrylamide derivative represented by the general formula (14) and a biotin derivative represented by the general formula (15).

Formula (14)

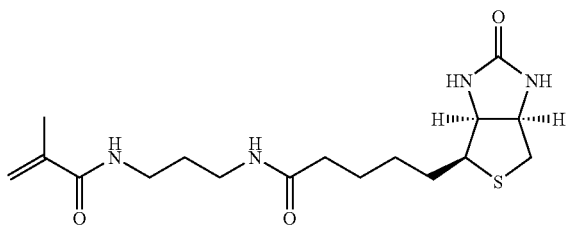

Formula (15)

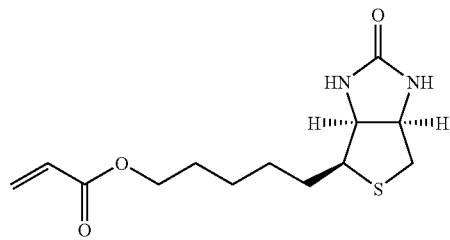

In addition, in order to control UCST, one or more other monomers selected from the aforementioned hydrophilic monomers and hydrophobic monomers can be used in the second UCST polymer of the invention similar to the case of the first UCST polymer of the invention.

The composition of respective monomers in polymerizing the second UCST polymer of the invention is not particularly limited, but it is generally monomer (1) :monomer having a biotin moiety or iminobiotin moiety: other monomer molar ratio=500 to 1:500 to 0.1:0 to 50, preferably 100 to 5:10:0.5:0 to 5.

Regarding a reaction solution containing the UCST polymer of the invention just after the polymerization, unreacted monomers, salts and the like impurities are present in the reaction solution. Elimination of the impurities may be carried out by dialysis, or it may be carried out by setting temperature of the solution to UCST or less to effect aggregation, recovering the aggregates and then removing the supernatant.

In each of the first and second UCST polymers of the invention, the molecular weight is not particularly limited, but it is desirable that the mass average molecular weight is within a range of from 500 to 1,000,000, more desirably within a range of from 1,000 to 100,000. Also, it is desirable that the UCST does not depend on said molecular weight.

Illustratively, the UCST according to the invention is a temperature when, after heating a UCST polymer-containing water prepared by adding the UCST polymer of the invention to water at a ratio of 1% by weight based on water to a clear state and then reducing temperature of the UCST polymer-containing water at a ratio of 1° C. per minute, visible light transmittance of said UCST polymer-containing water becomes ½ of the value at the time of the clear state.

There is a case in which visible light transmittance of said UCST polymer-containing water becomes ½ of the value at the time of the clear state, and the value of ½ is maintained within a certain temperature range when the temperature is further increased or reduced. The upper limit of this temperature range is called UCST at the time of temperature rising, and the lower limit thereof is called UCST at the time of temperature falling. The difference between them (temperature range) is called a switching range. This switching range may be as narrow as possible and is preferably 10° C. or less, more preferably 0° C., according to the invention.

Though UCST of the UCST polymer of the invention is not particularly limited, when the UCST polymer of the invention is used as a separating agent, it is preferably within a range of from 0 to 50° C., particularly preferably within a range of from 0 to 40° C.

The pair of substances mutually having specific action are substances which are specifically adsorbed to each other by an inter-ion interaction, hydrogen bond, a hydrophobic interaction, configuration to a metal atom and the like interactions, and illustrative examples of the combination include biotin and avidin, an antigen and its antibody, a polynucleotide and another polynucleotide having a complementary nucleotide sequence, cDNA and mRNA, an enzyme (active site) and its substrate, an enzyme (active site) and its product, an enzyme (active site) and its competitive inhibitor, an enzyme (coenzyme binding site) and its coenzyme, an enzyme (coenzyme binding site) and a triazine pigment, a protease and a protease inhibitor, an Fc region and protein A, an Fc region and protein G, lectin and a saccharide, a hormone receptor and the hormone, DNA and a DNA binding protein, heparin and fibronectin, heparin and laminin, polythymine and mRNA, an *Escherichia coli* antibody and *Escherichia coli*, and an antibody (IgG) and anti-IgG.

Among them, the combination of biotin and avidin can be used most desirably in the invention. When biotin is immobilized to the first UCST polymer of the invention, it becomes possible to separate and recover only an avidin-immobilized substance of interest selectively, and when avidin is immobilized to the first or second UCST polymer of the invention, it becomes possible to separate and recover only a biotin-immobilized substance of interest selectively.

In this connection, according to the invention, biotin may be iminobiotin, and avidin may be streptoavidin. The effect of the invention can be obtained in each case.

The substance of interest in that case is not particularly limited, but an enzyme, an antibody, a nucleic acid, a molecular chaperon, a heat shock protein and the like can be exemplified.

When avidin is immobilized to the UCST polymer of the invention, it is possible to keep the maximum of 3 sites among the 4 biotin-binding sites of avidin under opened state, so that it becomes possible to separate and recover a biotinylated substance of interest.

In reality however, it is difficult to immobilize avidin directly to the UCST polymer, so that it is desirable to immobilize avidin to the UCST polymer of the invention by linking avidin to biotin immobilized to the second UCST polymer of the invention.

When the UCST polymer of the invention to which one of a pair of substances mutually having specific action is immobilized is used, it becomes possible to easily separate and recover the other one of the substances or a substance to which said substance is immobilized.

For example, when the UCST polymer of the invention to which an enzyme is immobilized is used in the enzyme reaction, it is possible to convert its substrate at a more quick rate in comparison with the conventional enzyme reaction which uses immobilized enzyme. Though the enzyme to be used in that case is not particularly limited, its examples include an oxidation-reduction enzyme, a transferase, a hydrolase, a degrading enzyme, an isomerase, a synthase and the like.

Regarding a substance formed by the conversion of a substrate, the enzyme and said formed substance can be easily separated by reducing temperature of a solution containing the UCST polymer of the invention and said formed substance to effect precipitation of only said UCST polymer and then removing the precipitated said UCST polymer alone.

When the UCST polymer of the invention to which an antibody is immobilized is used, separation and concentration of a microorganism in a solution can be carried out efficiently. The antibody to be used in that case may be a monoclonal antibody or a polyclonal antibody.

The separation method or concentration method of a microorganism in a solution is not particularly limited, but its illustrative examples include a method in which said UCST polymer is added to a solution containing a microorganism, the microorganism and said UCST polymer are allowed to contact with each other sufficiently, and then only the UCST polymer to which the microorganism is adsorbed is precipitated by reducing temperature of said solution and the precipitated, UCST polymer alone is removed. According to this method, it is possible to separate and concentrate a microorganism in a solution easily.

For example, when the antibody to be used is a *Salmonella* antibody, the *Salmonella* strain alone in a food suspension can be separated and concentrated easily, so that it is possible to produce a high sensitivity microorganism inspection kit or a diagnostic drug by combining the UCST polymer of the invention to which an optional antibody is immobilized and an appropriate detection reagent.

Since magnetic fine particles prepared by immobilizing a molecular chaperone or heat shock protein to the UCST polymer increase stability of enzymes and antibodies in solutions, their repeated leaving becomes possible and they can assist protein production and material production at an industrial level. In general, molecular chaperone and the like proteins are expensive so that their use at an industrial level is difficult.

A method can be exemplified in which the UCST polymer of the invention to which a nucleic acid is immobilized is added to a solution containing a nucleic acid, the nucleic acid and said UCST polymer are allowed to contact with each other sufficiently, and then only the UCST polymer to which the nucleic acid is adsorbed is precipitated by reducing temperature of said solution and the precipitated UCST polymer alone is removed. According to this method, it is possible to easily separate and concentrate nucleic acid in the solution. It is possible also to apply said method for separating and concentrating nucleic acid to purification, concentration, detection and the like of a specified gene.

Also, purification, detection and concentration of an optional nucleic acid can be easily carried out by sufficiently carrying out hybridization in a mixed solution containing two or more kinds of nucleic acids and said UCST polymer, aggregating and recovering the nucleic acids by reducing temperature of said mixed solution and then increasing the temperature again.

For example, a DNA or mRNA of interest can be concentrated and purified by using a biotinylated DNA or biotinylated polythymine having a sequence complementary to the DNA of interest. By amplifying the thus obtained nucleic acid by various gene amplification methods, the nucleic acid can be detected with high sensitivity. Though the nucleic acid amplification method is not particularly limited, PCR method and RT-PCR method can be used in the invention suitably.

The method for immobilizing one of a pair of substances mutually having specific action to the first UCST polymer of the invention is not particularly limited, but a method in which one of said pair of substances is immobilized to already synthesized said UCST polymer (to be referred to as "immobilization method" hereinafter), a method in which one of said pair of substances, to which avidin is immobilized, is linked to the second UCST polymer of the invention making use of the specific reaction of avidin and biotin (to be referred to as "binding method" hereinafter) and the like can be exemplified.

As the aforementioned immobilization method, covalent bond is desirable, but it may also be a bonding making use of an ion complex or charge-transfer complex or a bonding making use of a biochemical affinity or the like.

In case that an antibody, enzyme or the like protein is linked to the UCST polymer of the invention, said UCST polymer and said protein may be linked together making use of reactivity of amino group, carboxyl group and the like functional groups possessed by said protein.

For example, when amino group of a protein is used, amido bond can be formed by the reaction formula shown below by introducing carboxyl group into said UCST polymer.

R: protein, R': UCST polymer

Also, the UCST polymer of the invention and a protein may be bonded using aldehyde group or epoxy group by the method shown below.

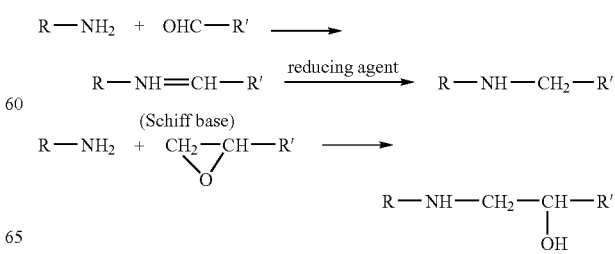

Also, when carboxyl group of said protein is used, amido bond can be formed by the reaction formula shown below by introducing amino group into the UCST polymer of the invention.

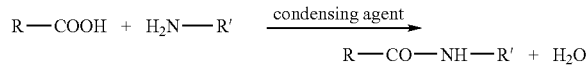

$$R—COOH + H_2N—R' \xrightarrow{\text{condensing agent}} R—CO—NH—R' + H_2O$$

In addition, an enzyme, antibody or the like protein can also be immobilized to said UCST polymer using an already known protein immobilization method which uses carbodiimide or the like, e.g., by designing the UCST polymer of the invention in such a manner that it has carboxyl group or the like functional group by copolymerization of carboxyl group of methacrylic acid or the like with the aforementioned monomer or other monomer.

When a protein is bonded to the UCST polymer of the invention by introducing an antibody, it is desirable that said bonding is carried out in a phosphate or Tris buffer having a pH value of around neutral. Also, the salt concentration can be optionally set depending on the purpose.

Regarding immobilization of one of a pair of substances mutually having specific action to the UCST polymer of the invention, one of a pair of substances mutually having specific action may be directly immobilized to said UCST polymer as described in the foregoing, but it is desirable to immobilize it to said UCST polymer via the bonding of biotin and avidin because of the easy immobilization operation. For example, an enzyme to which avidin is immobilized may be immobilized to the second UCST polymer of the invention to which biotin is immobilized, making use of the specific action between avidin and biotin.

More desirable is, e.g., to immobilize an enzyme to which biotin is immobilized to the UCST polymer to which avidin-linked biotin is immobilized. Since said avidin-linked biotin can immobilize 3 biotinylated enzyme molecules at the maximum as described in the foregoing, conversion, separation and recovery of the substrate can be made with more higher efficiency.

As a matter of course, this is not limited to enzymes and the similar effect can be obtained when they are the aforementioned pair of substances mutually having specific action.

The separating agent of the invention is not particularly limited with the proviso that it contains the UCST polymer of the invention, but containing ratio of said UCST polymer to the separating agent is preferably within the range of from 1 to 100% by weight, and particularly preferably within the range of from 2 to 30% by weight.

As the other component, ferrite particles, magnetite particles, hematite particles and the like can be exemplified.

When the separating agent of the invention is used, separation of microorganisms, nucleic acids, proteins, peptides, antigens, environmental hormones and the like can be carried out easily.

Regarding the UCST polymer of the invention, it is desirable that its UCST is not changed even in case that one of a pair of substances mutually having specific action is immobilized, and it is further desirable that its UCST is not changed even in case that dissolution and insolubilization steps are repeatedly carried out.

In addition, the UCST polymer of the invention can be applied particularly effectively to inspection drugs and diagnostic drugs such as detection of bacteria and residual agricultural chemicals, separation of bioproducts such as biomaterials of microorganisms and cell cultures, and activation and maintenance of biological reaction functions by immobilization of enzymes, molecular chaperones and the like.

EXAMPLES

The invention is described further in detail in the following examples, but the invention is not limited to these examples.

Example 1

Synthesis of N-acryloyl Glycine Amide

A 9 parts by mass portion of acrylic acid chloride and 11 parts by mass of glycine amide hydrochloride were suspended in 200 ml of ether and stirred at 10° C. for 3 hours. Thereafter, 100 ml of saturated sodium bicarbonate was added and the stirring was further carried out at room temperature for 1 hour. Next, 200 ml of ethyl acetate was added to carry out extraction of the organic phase. Said organic phase was concentrated under a reduced pressure, and the thus obtained residue was subjected to silica gel column chromatography using ethyl acetate as the mobile phase, thereby obtaining 10 parts by mass of a compound as white crystals. The thus obtained compound was analyzed by NMR and mass spectrometry to confirm that said compound is N-acryloyl glycine amide.

Example 2

Synthesis of UCST Polymer: (Copolymer of N-acryloyl Glycine Amide and N-acetyl Acrylamide (Molar Ratio 10:1)

A 13 parts by mass portion of N-acryloyl glycine amide and 1.1 parts by mass of N-acetyl acrylamide were dissolved in 100 ml of dimethyl sulfoxide and, using 0.1 part by mass of azobisisobutyronitrile (AIBN) as the initiator, polymerization was carried out for 3 hours in an atmosphere of nitrogen. After completion of the reaction, reprecipitation was carried out using ethanol to obtain a white polymer. By carrying out NMR analysis of the thus obtained polymer, it was confirmed that said polymer is a copolymer of N-acryloyl glycine amide and N-acetyl acrylamide. Also, when molecular weight was measured using a GPC, mass average molecular weight of said copolymer was about 6,000.

When the obtained polymer was dissolved in PBS saline buffer of pH=7.6 (2% by mass) and its UCST was measured in a quartz cell using a visible light of 500 nm, it was about 13° C. at the time of temperature rising and about 5° C. at the time of temperature falling.

Example 3

Synthesis of UCST Polymer: (Copolymer of N-acryloyl Glycine Amide and a Monomer According to General Formula (14) (to be Referred to as "Monomer (14)" Hereinafter (Molar Ratio 10:1)

A 13 parts by mass portion of N-acryloyl glycine amide and 3.7 parts by mass of monomer (14) were dissolved in 100 ml of dimethyl sulfoxide and, using 0.1 part by mass of AIBN as the initiator, polymerization was carried out for 3 hours in an atmosphere of nitrogen. After completion of the reaction, reprecipitation was carried out using ethanol to obtain a white polymer. By carrying out NMR analysis of the thus obtained polymer, it was confirmed that said polymer is a copolymer of N-acryloyl glycine amide and monomer (14). Also, when molecular weight was measured using a GPC, mass average molecular weight of said copolymer was about 8,000.

When the obtained polymer was dissolved in PBS saline buffer of pH=7.6 (2% by mass) and its UCST was measured in a quartz cell using a visible light of 500 nm, it was about 33° C. at the time of temperature rising and about 21° C. at the time of temperature falling.

Example 4

Specific Separation of Avidin from Albumin

A 5 mg portion of the UCST polymer obtained in Example 3, 50 (1 of 1.0% avidin solution, 100 (1 of 1.0 M sodium phosphate buffer (pH 7.0), 450 (1 of distilled water and 400 (1 of 2.5% albumin solution were thoroughly mixed in a test tube, and then said test tube was put in ice water to effect aggregation of the polymer by reducing temperature of the solution to UCST or less. A 100 (1 portion of the supernatant was taken out and subjected to denaturation treatment with SDS, and then it was confirmed by SDS-PAGE (SDS-polyacrylamide gel electrophoresis) that only the band corresponding to avidin was gone from the supernatant.

Example 5

Synthesis of UCST Polymer: (Copolymer of N-acryloyl Glycine Amide and Monomer (14) (Molar Ratio 200:1)

A 13 parts by mass portion of N-acryloyl glycine amide and 0.19 part by mass of monomer (14) were dissolved in 100 ml of dimethyl sulfoxide and, using 0.1 part by mass of AIBN as the initiator, polymerization was carried out for 3 hours in an atmosphere of nitrogen. After completion of the reaction, reprecipitation was carried out using ethanol to obtain a white polymer. By carrying out NMR analysis of the thus obtained polymer, it was confirmed that said polymer is a copolymer of N-acryloyl glycine amide and monomer (14). Also, when molecular weight was measured using a GPC, mass average molecular weight of said copolymer was about 8,000.

When the obtained copolymer was dissolved in PBS saline buffer of pH=7.6 (2% by mass) and its UCST was measured in a quartz cell using a visible light of 500 nm, it was about 18° C. at the time of temperature rising and about 7° C. at the time of temperature falling.

Example 6

Immobilization of Avidin-immobilized Enzyme to UCST Polymer

A 3 mg portion of the UCST polymer obtained in Example 5, 1,000 µl of a commercially available avidin-immobilized peroxidase solution (1 mg/ml) and 100 µl of 1.0 M sodium phosphate buffer (pH=7.0) were added to 700 µl of distilled water and thoroughly mixed. The thus obtained solution was cooled to a temperature of UCST or less and the formed aggregate was recovered to which, after removing 1,900 µl of the supernatant, was subsequently added 1,900 µl of 0.1 M phosphate buffer (pH=7.0), thereby preparing a solution containing the UCST polymer to which the avidin-immobilized peroxidase was immobilized.

Said UCST polymer dissolved in said solution when temperature of said solution exceeded UCST and aggregated when it was UCST or less. By changing temperature of said solution using a thermostat, dissolution, aggregation and centrifugation were carried out, and peroxidase activity in the supernatant at each stage was measured by the peroxidase activity measuring method shown below. In this case, after recovery of the aggregate by centrifugation, 1,900 µl of the supernatant at each stage was removed and 1,900 µl of 0.1 M phosphate buffer (pH=7.0) was added.

Results of the measurement of peroxidase activity in the supernatants when aggregation and dissolution were repeatedly carried out by the above method are shown in Table 1. In this connection, the peroxidase activity was expressed by specific activity when the activity at the time of the first dissolution was defined as 100.

(Peroxidase Activity Measuring Method)

A 100 µl portion of 100 mM hydrogen peroxide, 100 µl of 50 mM phenol, 100 µl of 50 mM 4-aminoantipyrine, 100 µl of 1.0 M sodium phosphate buffer (pH=7.0) and 580 µl of distilled water were mixed in advance in the cell of an absorptiometer, 20 µl of each sample was added to said cell and thoroughly mixed again, and then peroxidase activity of said sample was calculated by measuring visible light absorbance of the formed substance at 500 nm. In this connection, the above operations were carried out at 30° C.

TABLE 1

| Repetition frequency (times) | Peroxidase activity (%) at the time of UCST polymer dissolution | Peroxidase activity (%) in supernatant after aggregation and recovery of UCST polymer |
|---|---|---|
| 1 | 100 | 15 |
| 2 | 98 | 10 |
| 3 | 95 | 7 |
| 5 | 95 | 6 |
| 10 | 91 | 3 |
| 20 | 80 | 0 |

It is evident from these results that activity of the avidin-immobilized peroxidase is hardly reduced even when dissolution and aggregation of said UCST polymer are carried out repeatedly.

Example 7

Immobilization of Biotin-immobilized Enzyme to Avidin-immobilized UCST Polymer

Firstly, in order to obtain an avidin-immobilized UCST polymer in such a state that three biotin-binding sites of avidin are opened, 5 mg of the UCST polymer obtained in Example 5 was thoroughly mixed in a test tube with 500 µl of 1.0% avidin solution, 100 µl of 1.0 M sodium phosphate buffer (pH=7.0) and 350 µl of distilled water, and then the tube was put in ice water to cooled temperature of said mixed solution to UCST or less, thereby effecting aggregation of said UCST polymer. After centrifugation of said aggregate, suction filtration was carried out to obtain a solution containing the avidin-immobilized UCST polymer in which biotin-binding sites other than the binding site with UCST polymer are opened.

To this solution containing the avidin-immobilized UCST polymer were added 1,000 µl of a commercially available biotin-immobilized peroxidase solution (1 mg/ml), 100 µl of 1.0 M sodium phosphate buffer (pH=7.0) and 700 µl of distilled water and thoroughly mixed. The thus obtained mixed solution was cooled, the formed aggregate was recovered, 1,900 µl of the supernatant was removed from said mixed solution after recovery, and then 1,900 µl of 0.1 M phosphate buffer (pH=7.0) was added to said mixed solution, thereby preparing the avidin-immobilized UCST polymer to which the biotin-immobilized peroxidase was immobilized. Using this UCST polymer, dissolution, aggregation and recovery were repeated in the same manner as in Example 6, and the peroxidase activity in the supernatants was measured, with the results shown in Table 2. In this connection, the peroxidase activity was also expressed by specific activity when the activity at the time of the first dissolution was defined as 100.

TABLE 2

| Repetition frequency (times) | Peroxidase activity (%) at the time of UCST polymer dissolution | Peroxidase activity (%) in supernatant after aggregation and recovery of UCST polymer |
|---|---|---|
| 1 | 100 | 2 |
| 2 | 98 | 1 |
| 3 | 96 | 1 |
| 5 | 98 | 0 |
| 10 | 94 | 0 |
| 20 | 90 | 0 |

It is evident that activity of the biotin-immobilized peroxidase immobilized to the avidin-immobilized UCST is hardly reduced even when dissolution and aggregation of said UCST polymer are carried out repeatedly.

Example 8

Immobilization of Heat Shock Protein to UCST Polymer

A 0.5 mg portion of a commercially available heat shock protein HSP70 to which biotin was immobilized was thoroughly mixed with 1 ml of 100 mM sodium phosphate buffer (pH=7.0), 5 µl of this mixed solution was taken out and subjected to denaturation treatment, and then the band of HSP70 was confirmed by SDS-PAGE.

Next, 500 µl of the biotinylated HSP70 sodium phosphate buffer solution was added to 5 mg of the avidin-immobilized UCST polymer prepared in Example 7 and thoroughly mixed, the mixed solution was cooled, and the aggregate formed by cooling was recovered to verify the presence of HSP70 in the supernatant by SDS-PAGE, thereby confirming that HSP70 was not present in the supernatant but the HSP70 was linked to avidin immobilized to the UCST polymer.

Example 9

Method for Separating and Concentrating Microorganism

A commercially available biotin-immobilized *Salmonella* antibody was immobilized to the UCST polymer in accordance with the method described in Example 7. Confirmation of the immobilization was carried out using SDS-PAGE. Next, 5 mg of said UCST polymer was added to 20 ml of a cell suspension prepared by adjusting said biotin-immobilized *Salmonella* strain to a concentration of 1 cell/ml and thoroughly stirred, the thus obtained mixed suspension was cooled to effect aggregation, of said UCST polymer, said aggregate was precipitated by centrifugation to remove the supernatant, and then the aggregate as the residue was adjusted to a volume of 1 ml by adding water. This aggregate-containing solution was added to 20 ml of the brain heart infusion agar medium which had been sterilized and incubated at 50° C. in advance, quickly mixed, spread on a plate, spontaneously cooled until agar was solidified and then incubated at 37° C. for 48 hours. Results of the counting of colonies after 48 hours are shown in Table 3. In this connection, all of these operations were carried out in a clean bench. Also, the number of cells in 1 ml of the initially prepared cell suspension without adding said UCST polymer was measured as a control in the same manner.

TABLE 3

|  | Control | Using UCST polymer |
|---|---|---|
| The number of colonies | 1 | 19 |

It is evident from these results that the *Salmonella* cells are concentrated by said UCST polymer.

Example 10

Immobilization of Nucleic Acid to UCST Polymer

A 450 µl portion of distilled water and 5 mg of the avidin-immobilized UCST polymer prepared in Example 7 were added to 500 µl of commercially available biotin-immobilized DNA fragments (50 to 1,000 bp) and thoroughly mixed, said mixed solution was cooled to effect aggregation of said UCST polymer, and then said aggregate was recovered by centrifugation. When DNA fragments in the supernatant were checked by an agarose gel electrophoresis, it was suggested that all of the DNA fragments are linked to said UCST polymer. The same test was carried out also on RNA to confirm that it is bonding to said UCST polymer.

While the invention has been described in detail and with reference to specific embodiments thereof, it will be apparent to one skilled in the art that various changes and modifications can be made therein without departing from the spirit and scope thereof.

This application is based on Japanese patent application No. 2000-249818 filed on Aug. 21, 2000, the entire contents thereof being hereby incorporated by reference.

INDUSTRIAL APPLICABILITY

The UCST polymer of the invention has UCST even in buffer solutions, and when the polymer of the invention is used, separation and concentration of microorganisms, purification, detection or concentration of nucleic acids, separation of biomaterials and conversion of materials can be carried out efficiently. It can be effectively used particularly in the separation, purification, immobilized enzymes, calibration and control of substances having a difficulty in setting temperature and substances which are unfitted for high temperature environment (e.g., bioproducts, enzymes, antibodies and the like proteins), or in chemovalves, drug delivery systems (DDS) and the like.

The invention claimed is:

1. A polymer obtained by polymerizing at least a monomer represented by general formula (1):

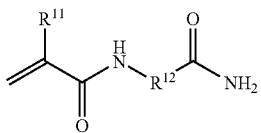

General formula (1)

wherein $R^{11}$ represents hydrogen atom or methyl group, and $R^{12}$ represents single bond or a straight or branched alkylene group having from 1 to 5 carbon atoms, and a monomer represented by general formula (2):

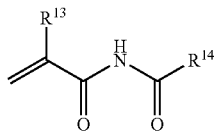

General formula (2)

wherein $R^{13}$ represents hydrogen atom or methyl group, and $R^{14}$ represents hydrogen atom, a straight, branched or cyclic alkyl group, alkoxyl group or alkylamino group having from 1 to 10 carbon atoms, an aryl group or a heterocyclic group, and wherein the polymer has a UCST.

2. A polymer obtained by polymerizing a monomer represented by general formula (I):

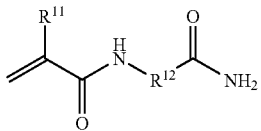

General formula (1)

wherein $R^{11}$ represents hydrogen atom or methyl group, and $R^{12}$ represents single bond or a straight or branched alkylene group having from 1 to 5 carbon atoms, and a monomer represented by general formula (4):

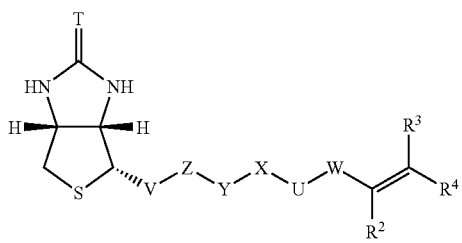

General Formula (4)

wherein $R^2$ represents hydrogen atom or an alkyl group, $R^3$ and $R^4$ each independently represents hydrogen atom, an alkyl group or an aryl group, T represents oxygen atom or =NH group, W represents single bond or carbonyl group, thiocarbonyl group or an alkylene group having from 1 to 5 carbon atoms, U represents single bond or —NH— group, X represents single bond or hydrocarbon bond having from 1 to 8 carbon atoms, oxygen atom or —NH— group, Y represents single bond or carbonyl group, thiocarbonyl group, —NH— group, 1,2-dioxyethylene group or 1,2-diaminoethylene group, Z represents single bond or carbonyl group, thiocarbonyl group, an alkylene group having from 1 to 5 carbon atoms, oxygen atom or —NH— group, and V represents single bond or an alkylene group having from 1 to 5 carbon atoms, and wherein the polymer has a UCST.

3. The polymer according to claim 1 or 2, wherein the polymer is further copolymerized with a hydrophilic monomer or a hydrophobic monomer other than those represented by general formulae (1), (2) and (4).

4. A polymer obtained by
   (1) copolymerizing the at least two species of monomers as set forth in either claim 1 or claim 2 with another monomer having a functional group, wherein one of a pair of substances mutually having specific action is immobilized to the monomer via the functional group, or
   (2) copolymerizing the at least two species of monomers as set forth in either claim 1 or claim 2 with another monomer having a functional group, and thereafter immobilizing one of a pair of substances mutually having specific action via the functional group.

5. The polymer according to claim 4, wherein the pair of substances mutually having specific action are one or more pairs selected from the combinations of biotin and avidin, an antigen and its antibody, a polynucleotide and another polynucleotide having a complementary nucleotide sequence, cDNA and mRNA, an enzyme (active site) and its substrate, an enzyme (active site) and its product, an enzyme (active site) and its competitive inhibitor, an enzyme (coenzyme binding site) and its coenzyme, an enzyme (coenzyme binding site) and a triazine pigment, a protease and a protease inhibitor, an Fc region and protein A, an Fc region and protein G, lectin and a saccharide, a hormone receptor and the hormone, DNA and a DNA binding protein, heparin and fibronectin, and heparin and laminin.

6. The polymer according to claim 4, wherein the pair of substances mutually having specific action are biotin and avidin.

7. The polymer according to claim 4, wherein one of said pair of substances, immobilized to the polymer, is biotin.

8. The polymer according to claim 7, wherein the biotin is linked to avidin.

9. The polymer according to claim 7, wherein an avidinylated enzyme is linked to biotin.

10. The polymer according to claim 8, wherein a biotinylated enzyme is linked to avidin-linked biotin.

11. A method for converting a substrate into a converted material and recovering said converted material, comprising
    mixing the polymer according to claim 9 and a substrate for the enzyme which is linked to biotin and therefore immobilized on the polymer to create a polymer solution, in which the enzyme and the substrate react,
    aggregating the polymer to which the enzyme is linked by cooling the polymer solution to a temperature not exceeding the UCST of the polymer,
    precipitating the aggregated polymer to separate and recover a supernatant solution comprising a converted material, wherein the converted material results from the reaction between the enzyme and the substrate.

12. The polymer according to claim 7, wherein an avidinylated antibody is linked to biotin.

13. The polymer according to claim 8, wherein a biotinylated antibody is linked to avidin-linked biotin.

14. A method for separating and concentrating a microorganism from a microorganism solution, comprising adding a polymer according to claim 12 to a solution comprising a microorganism, aggregating the polymer by cooling the polymer solution to a temperature not exceeding the UCST of the polymer, and precipitating and recovering the microorganism captured by the polymer.

15. The polymer according to claim 7, wherein an avidinylated molecular chaperone is linked to biotin.

16. The polymer according to claim 8, wherein a biotinylated molecular chaperone is linked to avidin-linked biotin.

17. A method for recovering a denatured protein, comprising adding the polymer according to claim 15 to a solution comprising a denatured protein, regenerating the protein, aggregating the polymer by cooling the polymer solution to a temperature not exceeding the UCST of the polymer, and separating and recovering the regenerated protein.

18. The polymer according to claim 7, wherein an avidinylated heat shock protein is linked to biotin.

19. The polymer according to claim 8, wherein a biotinylated heat shock protein is linked to avidin-linked biotin.

20. A method for recovering a denatured protein, comprising adding the polymer according to claim 19 to a solution comprising a denatured protein, regenerating the protein, aggregating the polymer by cooling the polymer solution to a temperature not exceeding the UCST of the polymer, and separating and recovering the regenerated protein.

21. The polymer according to claim 7, wherein an avidinylated nucleic acid is linked to biotin.

22. The polymer according to claim 8, wherein a biotinylated nucleic acid is linked to avidin-linked biotin.

23. A method of recovering and concentrating nucleic acid from a nucleic acid solution comprising adding the polymer according to claim 21 to a solution containing nucleic acid, allowing the nucleic acid to complimentarily bond to the polymer, aggregating the polymer by cooling the polymer solution to a temperature not exceeding the UCST of the polymer, and precipitating and recovering the nucleic acid captured by the polymer.

24. A method for detecting a nucleic acid, comprising directly employing or amplifying the nucleic acid after it is recovered by the method according to claim 23, and detecting the nucleic acid by gel electrophoresis.

25. The method for detecting a nucleic acid according to claim 24, wherein the amplifying method is a PCR method or an RT-PCR method.

26. A separating agent comprising at least two components, one of which is a polymer according to claim 2.

27. A method for separating a biomaterial, comprising adding the separating agent according to claim 26 to a solution containing a biomaterial, aggregating the separating agent by cooling to a temperature not exceeding the UCST of the polymer, and separating and recovering the biomaterial.

28. A polymer obtained by polymerizing a monomer immobilizing one of a pair of substances mutually having specific action and a monomer component constituting the polymer according to claim 3.

29. A method for converting a substrate into a converted material and recovering said converted material, comprising
   mixing the polymer according to claim 10 and a substrate for the enzyme which is linked to avidin-linked biotin and therefore immobilized on the polymer to create a polymer solution, in which the enzyme and the substrate react,
   aggregating the polymer to which the enzyme is linked by cooling the polymer solution to a temperature not exceeding the UCST of the polymer,
   precipitating the aggregated polymer to separate and recover a supernatant solution comprising a converted material, wherein the converted material results from the reaction between the enzyme and the substrate.

30. A method for separating and concentrating a microorganism from a microorganism solution, comprising adding a polymer according to claim 13 to a solution comprising a microorganism, aggregating the polymer by cooling the polymer solution to a temperature not exceeding the UCST of the polymer, and precipitating and recovering the microorganism captured by the polymer.

31. A method for recovering a denatured protein, comprising adding the polymer according to claim 16 to a solution comprising a denatured protein, regenerating the protein, aggregating the polymer by cooling the polymer solution to a temperature not exceeding the UCST of the polymer, and separating and recovering the regenerated protein.

32. A method of recovering and concentrating nucleic acid from a nucleic acid solution comprising adding the polymer according to claim 22 to a solution containing nucleic acid, allowing the nucleic acid to complimentarily bond to the polymer, aggregating the polymer by cooling the polymer solution to a temperature not exceeding the UCST of the polymer, and precipitating and recovering the nucleic acid captured by the polymer.

* * * * *